United States Patent [19]

Goldowsky

[11] 4,136,692

[45] Jan. 30, 1979

[54] FLOW METER ADMINISTRATION DEVICE

[76] Inventor: Michael Goldowsky, 7 Greenwood La., Valhalla, N.Y. 10595

[21] Appl. No.: 765,561

[22] Filed: Feb. 4, 1977

Related U.S. Application Data

[63] Continuation-in-part of Ser. No. 659,220, Feb. 19, 1976, abandoned.

[51] Int. Cl.$^2$ .............................................. A61M 5/16
[52] U.S. Cl. ............................ 128/214 C; 128/214.2; 73/215; 137/551; 222/40; 222/159
[58] Field of Search ............ 128/214 R, 214 C, 214.2; 73/194 R, 198, 215, 216; 222/23, 40, 159; 137/551

[56] References Cited

U.S. PATENT DOCUMENTS

| | | | |
|---|---|---|---|
| 2,479,786 | 8/1949 | Stevens | 73/216 |
| 3,340,871 | 9/1967 | Jellies | 128/214 C |
| 3,835,885 | 9/1974 | Kreyenberg | 137/551 |
| 3,929,157 | 12/1975 | Serur | 128/214 C X |
| 3,993,066 | 11/1976 | Virag | 128/214 C |

FOREIGN PATENT DOCUMENTS 398490 9/1933 United Kingdom ...................... 73/216

*Primary Examiner*—Dalton L. Truluck

[57] ABSTRACT

A flow meter for liquids comprising two tubes interconnected at their lower ends, one tube providing an inflow passage for liquid from a supply container and the second tube having an opening at its upper end. A thin orifice disc in sealing engagement with lower portions of the tubes has an orifice through which liquid flows, the rate of flow being governed by flow control means associated with a set incorporating the flow meter. The tubes are enclosed within a drip chamber having an outlet at its lower end. Indicia associated with the second tube mark the various flow rates. In another form of the device, a third tube adjacent the second tube and connected by their top portions with a passageway has a second orifice at its base and second indicia so that a flow meter with an extended flow rate capability is obtained. The flow meters provide greater accuracy in flow rates and the flow rates are only minimally affected by solutions of widely differing viscosities.

11 Claims, 9 Drawing Figures

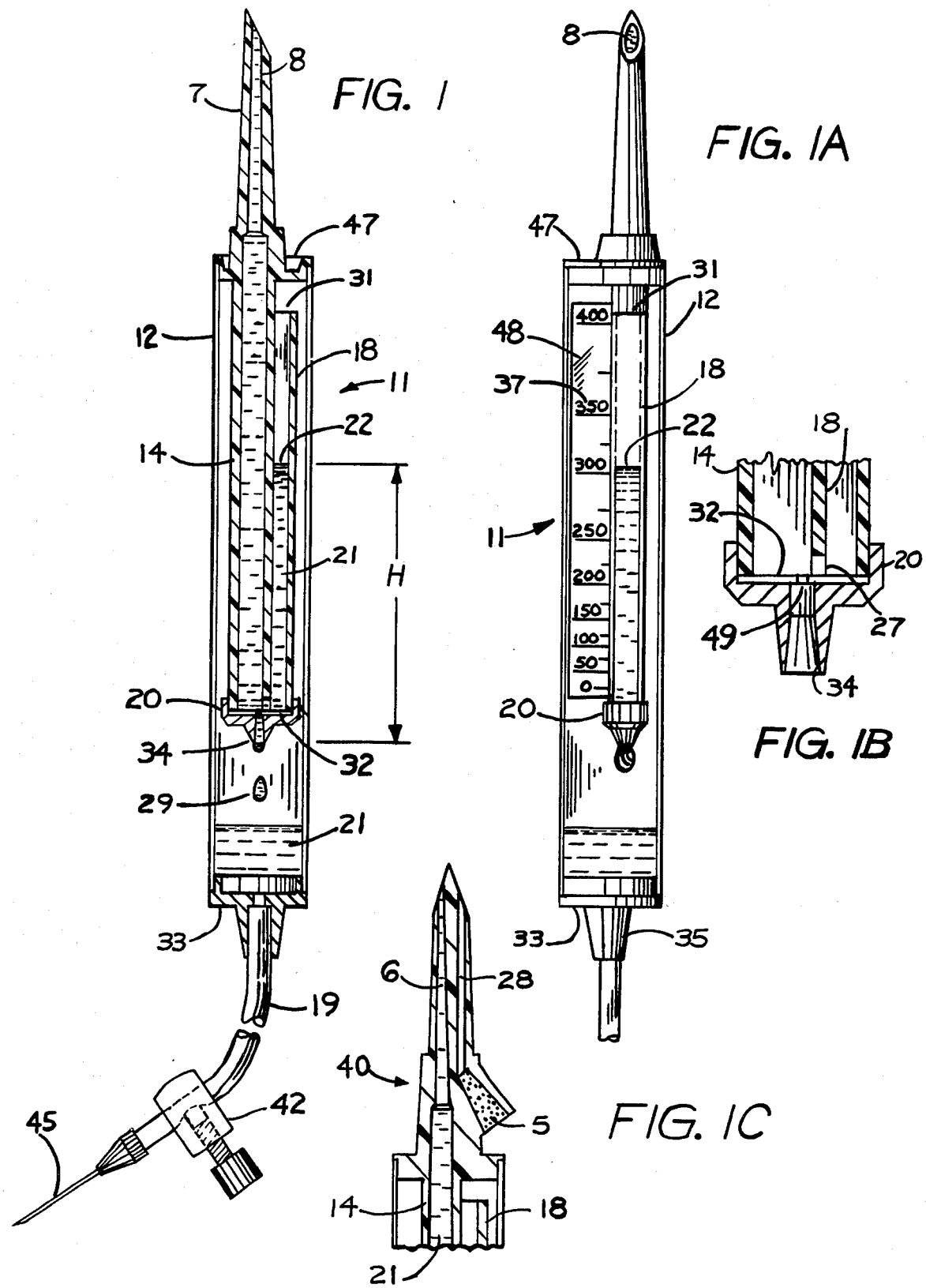

FLOW METER ADMINISTRATION DEVICE

This is a continuation-in-part of abandoned application Ser. No. 659,220, filed Feb. 19, 1976.

BACKGROUND OF THE INVENTION

This invention relates primarily to flow indicating devices and more particularly to improved flow meters for parenteral solution administration wherein greater uniformity of flow rates are achieved regardless of viscosity or density of the solutions.

Parenteral administration sets are generally used to infuse various types of solutions into a patient. The administration set provides a sterile passage for a physiological fluid in a supply container, e.g. sterile water, saline, or various concentrations of glucose solution, etc. Conventional intravenous sets employ a closed drip chamber with a drip nozzle whose main function is to enable the rate of flow to be calculated by observing the number of drops per unit time. This is not only time consuming but inaccurate. On the one hand drop size changes with flow rate and on the other, conversion of drop timing to drip rate is difficult.

A number of flow meters have been designed in an attempt to improve on the accuracy and speed in determining flow rates. They generally employ a small ball of proper specific gravity positioned within a tapered vertical tube. The ball, which has a specific gravity greater than that of the fluid, rises to a larger cross sectional area of the indicating tube as the fluid flows upwardly in the tube. The position of the ball relative to a calibrated scale indicates the flow rate of solution through the set. Some rotameter devices employ a light weight float, but the principle of operation is the same.

The advantages of these prior art flow meter devices over conventional drip sets noted above, is that flow rate can be more accurately and quickly set. Furthermore, a change in flow is readily apparent during a long term infusion and can be readily adjusted by the nurse.

Major disadvantages of these flow meter devices are the high cost and the inability to manufacture the flow indicating tapered tube and ball to the required tolerances to achieve sufficient flow accuracy. High volume production is not feasible for moulding plastic parts to sub-thousandths of an inch accuracy requirements. Selective assembly of components has also been tried but results in excessive assembly time and cost.

A major performance disadvantage of these rotameter type flow meters lies in the fact that they are sensitive to fluid viscosity, density, and temperature. Consequently, these devices are generally only accurate for one type of fluid at a known temperature. This is due to the fact that the larger the fluid viscosity the larger the drag force on the ball and the larger the fluid density, the greater the momentum force across the ball. Increases in these parameters cause the ball to travel higher up the tube at the same flow rate, thereby producing error.

Temperature changes primarily affect the viscosity of solutions with the drag force increasing as temperature decreases. For these reasons fluid calibration curves are usually supplied with industrial type devices. This is not practical nor desired in hospital application. For example, a flow meter of this type will not read accurately for 20% glucose solutions which are quite viscous if the flow meter device had been calibrated for less viscous 5% glucose solutions.

Furthermore, dimensional changes in the typically plastic parts after moulding or during storage prior to shipment affects the accuracy of the device. Warpage or locked in stresses gradually relax inducing undesireable strains. Also, the complexity of present moving element flow meter devices results in a substantial number of parts, typically in excess of 20, which unavoidably adds to assembly time and increased cost to the point that most hospitals cannot afford the extra cost for other than certain specialty applications such as pediatric use.

Another type of flow meter device has been disclosed by D. S. Stevens in U.S. Pat. No. 2,479,786. His device comprises a glass tube bent back upon itself similar in shape to a "J" and with a hole in the wall of the tube at the bent portion leading into the shorter leg. The tube is encased in an enlarged tubular body having an outlet. A liquid flowing into the tube rises into the shorter leg of the tube and flows slowly through the hole in the bend and subsequently through the outlet. The height which the liquid reaches in the shorter leg is set by regulating a stopcock located between a solution supply container and the flow meter. Indicia on the shorter leg mark the various flow rates for the device. Although the design of this type flow meter is relatively simple as compared to the rotameter type described above, in tests conducted with a model constructed as disclosed, flow rates also substantially varied depending on the viscosity of the solutions used. A major problem with this flow meter is the inability for making holes of uniform size and shape in the glass tube of large numbers of the flow meter, thus substantially affecting the calibration of one device to the other. It would be difficult if not impossible to make holes of uniform diameter throughout the length of the hole.

Accordingly, a primary object of the present invention is to provide a flow meter device which affords more uniform flow rates for various types of fluids of differing viscosity and density, and upon which temperature changes has little effect.

Another object of the present invention is to provide a flow meter which will permit rapid and accurate indications of flow rates.

Another object of the present invention is to provide an improved flow meter whose functioning parts can be made with close tolerances so as to provide uniform reliability of use in production quantities of the device.

Yet another object of the present invention is to provide an improved flow meter of simplified construction capable of high volume production at low cost.

SUMMARY OF THE INVENTION

These and other objects are accomplished by a flow meter device of the present invention which comprises a first fluid passage means having its upper end in communication with a supply container for liquid and its lower end in communication with a second fluid passage means, both passage means being contained within a chamber having an outlet at its lower portion. The distinguishing characteristic of the flow meter of this invention is the provision of a discrete orifice as provided by a thin orifice plate or disc positioned at a lower wall portion of the passage means. Liquid flowing into and through the first fluid passage means will rise upwardly into the second fluid passage means to a height governed by the size of the orifice and by the amount of entering liquid as regulated by a flow control device. Calibrated indicia associated with the second fluid passage means allows one to determine rapidly and accurately the rate of flow of any liquid passing through the orifice.

In an alternative form of the device which provides the capability for an extended range of flow rate indication, a third fluid passage means is included adjacent the second fluid passage means, both being connected at their top portions and with a second discrete orifice at the lower end of the third passage means. A higher flow rate range is indicated by calibrations associated with the third passage means and a lower flow rate range is indicated with the second passage means.

I have found that if the orifice in the flow meter of the present invention is properly formed, it is then possible to provide large quantities of the flow meter having substantially identical flow rates as indicated on identical flow rate scales or indicia. Heretofore, such capability for replication of identically functioning flow meters has not been possible, the prior art devices having differences in flow rates from one flow meter to another as a consequence of uncontrollable variability which is inherent in the formation of the critical parts. What I have particularly been able to accomplish is to provide a flow meter which will indicate substantially the same flow rates regardless of the viscosity or density of the liquids passing through them. This characteristic is not possible with any of the prior art devices. Such a capability becomes quite critical in many operations particularly in the administration of parenteral fluids since such fluids vary so widely in their viscosities and densities.

I have found the objects of the present invention can be achieved by providing an orifice plate or disc which is very thin and having the property of allowing discrete holes or orifices to be formed in the disc which can be held to tight tolerances with respect to size.

Rates of flow of liquids through a true or theoretical orifice, i.e., an orifice having no thickness, is expressed by the equation $$Q = C_D A [\sqrt{2g\Delta P/d}] \quad (1)$$

where Q is rate of fluid flow in cubic inches per second, $C_D$ is the dimensionless discharge coefficient, A is the cross sectional area of the orifice in square inches, g is gravity in units of 384 inches per second square, $\Delta P$ is pressure across the orifice in pounds per square inch and d is the density of the fluid in pounds per cubic inch. Since $\Delta P = dH$, this equation can be simplified to $$Q = C_D A \sqrt{2gH} \quad (2)$$

where H is the height in inches from the orifice to the top of a column of liquid above the orifice. Equation (2) clearly demonstrates that height H is dependent only upon flow rate Q and orifice area A and not upon viscosity or density.

Although viscosity and density factors do not apply in a consideration of flow rates through a theoretical orifice, I have found these factors cannot be ignored with a flow meter device is constructed where orifice thickness is not carefully controlled as in the flow meter of Stevens discussed supra. Of course, a flow meter having an orifice with no thickness (i.e. theoretical orifice) cannot be constructed. However, I have determined that within practical limitations a flow meter can be made so that effects of viscosity and density are minimized whereby percentage errors in flow rates are greatly decreased to acceptable levels when solutions of differing viscosities are used.

In comparing a specific flow rate of water with that of a solution having a different viscosity, the percentage of error or the difference in flow rates when orifices of different thickness are used can be calculated by using the following equation for rates of flow typically encountered in solutions for intravenous infusions. Equation (3) can be derived theoretically by taking into account the pressure loss along the orifice as a function of Reynolds number for this highly viscous flow.

$$\% \text{ error in flow rate} = 609 \, C_D^2 \sqrt{t}/q \, (\sqrt{\nu_1} - \sqrt{\nu_2}) \quad (3)$$

where t = orifice thickness in inches
Q = rate of flow (in.$^3$/sec.)
$\nu_1$ = kinematic viscosity of solution 1 (in.$^2$/sec.)
$\nu_2$ = kinematic viscosity of solution 2 (in.$^2$/sec.)

The discharge coefficient $C_D$ is essentially constant for thin orifice plates and it can be determined for any orifice by experimentation with flow meters constructed according to a design which will be described henceforth in greater detail. By using equation (2) supra, $C_D$ values can thus be calculated since values for Q, A and H can be measured. For example, in a typical experiment using water in flow meters with a 0.001 inch thick orifice and a 0.035 inch long hole of equal diameters (0.0145 inch), a $C_D$ of 0.715 for the 0.001 inch orifice and a $C_D$ of 0.60 for the 0.035 inch orifice were obtained. The 0.035 inch orifice disc approximates the wall thickness of glass tubing which characterizes the Stevens flow meter described in U.S. Pat. No. 2,479,786.

Using known kinematic viscosity values ($\nu$) of 7.26 × 10$^{-3}$, 2.73 × 10$^{-3}$ and 1.55 × 10$^{-3}$ for 40% and 20% glucose and water, respectively, as a typical example, the following theoretical percent error in flow rate may thus be calculated:

TABLE 1

| Flow Rate, Q | % Flow Rate Error 20% glucose | | 40% glucose | |
|---|---|---|---|---|
| (cc/hr) | t = .001" | t = .035" | t = .001" | t = .035" |
| 50 | 3.3% | 13.7% | 11.8% | 49.3% |
| 100 | 2.4% | 10.0% | 8.4% | 34.9% |
| 200 | 1.7% | 7.1% | 6.0% | 24.9% |
| 300 | 1.4% | 5.8% | 4.9% | 20.0% |
| 400 | 1.2% | 5.0% | 4.2% | 17.4% |

In actual experiments where flow rates for 20% glucose solution and water were measured from flow meters having 0.001 and 0.035 inch thick orifice discs, values very close to the theoretical for flow rate error were observed. For example, at a flow rate of 100 cc/hr., 20% glucose had a flow rate only 0.4 percent slower in the flow meter with a 0.001 inch orifice disc. With a 0.035 inch orifice disc, the flow rate of 20% glucose was 9.0 percent slower.

In another experiment using stainless steel orifice discs of the same thickness and each having an orifice diameter of 0.0135 inch, the following results were obtained on water and a 10% Dextran 40 solution (kinematic viscosity value = 9.3 × 10$^{-3}$):

TABLE 2

| Flow Rate, Q | % Flow Rate Error 10% Dextran, Theoret. | | 10% Dextran, Actual | |
|---|---|---|---|---|
| (cc/hr) | t = .001" | t = .035" | t = .001" | t = .035" |
| 180 | | 47.0% | | 47.0% |
| 260 | | 39.0% | | 37.0% |

TABLE 2-continued

| Flow Rate, Q | % Flow Rate Error | | | |
|---|---|---|---|---|
| | 10% Dextran, Theoret. | | 10% Dextran, Actual | |
| (cc/hr) | t = .001" | t = .035" | t = .001" | t = .035" |
| 109 | 9.0% | | 10.1% | |

In calculating the theoretical values above for % error in flow rates using equation (3), $C_D$ values determined experimentally were 0.55 and 0.63 for the 0.001 and 0.035 inch orifice discs, respectively. It is readily apparent that even with 10% Dextran 40 solution, which is a frequently used parenteral solution having a very high viscosity, the percent error in flow rate is quite acceptable when a flow meter with a thin orifice disc is used. A flow meter with a thick orifice disc, however, would not be acceptable.

I have found the thickness of the disc or plate in which the orifice is formed should be very little more than 0.015 inch, preferably no more than about 0.005 inch and more preferalby about 0.001 inch or less. The thinner the disc, the smaller the flow rate errors which are obtained when using solutions of differing viscosities. For discs substantially thicker than 0.015 inch, flow meter errors are not acceptable for solutions usually encountered in intravenous administration.

Preferred materials for the orifice disc or plate are materials which are unaffected by temperature changes or other conditions which might alter orifice size and which can be readily manipulated so that orifices of uniform diameter can be repetitively formed. Included in such materials are, for example, metals, ceramics and certain thermosetting plastics. Preferred are metal discs, such as, for example, stainless steel discs; stainless steel is corrosion resistant and uniformly sized orifices can be readily made by laser drilling.

To illustrate the necessity for an accurately sized orifice, orifice area $\pi D^2/4$ is substituted for A in equation (2) where D is the orifice diameter is inches. The level of fluid in the indicating tube which gives the flow rate is seen to depend directly on the orifice diameter to the second power. Thus, an error of 0.5% in orifice diameter results in an indicia flow rate error of two times this value or 1%.

Substituting in equation (2) a typical rapid flow rate such as 400 cc per hour (0.0068 cubic inch per sec.) occurring at a scale height H of 3 inches, for example, using a typical discharge coefficient of 0.715, gives a solved for orifice diameter of 0.016 inch. For lower rates of flow, as 120 cc/hr. full scale such as is used in pediatric care, the orifice diameter should be considerably smaller, generally in the range of 0.005 to 0.01 inch.

Several methods can be employed to obtain large quantities of orifice discs having substantially the same size orifice so that production quantities of the flow meter device can be made where there will be no variation in flow rates from one meter to another. The orifices may be formed by drilling, punching, photochemical etching, or by the use of laser beams. Laser beam fabrication of orifices can routinely hold tolerances of about 100 micro inch in diameter representing 0.6% diameter error. This corresponds to a flow rate inaccuracy of only 1.2%, which is generally more accurate than required for parenteral infusion and most industrial applications.

BRIEF DESCRIPTION OF THE DRAWINGS

Other objects and advantageous features of the invention will be apparent in a description of specific embodiments thereof and described hereinafter with reference to the accompanying drawings, in which:

FIG. 1 is a sectional view of a fluid flow meter device according to the present invention;

FIG. 1A is a view of the flow meter device of the present invention showing in particular the calibrated flow rate scale and indicating fluid column;

FIG. 1B is an enlarged sectional view of the nozzle and orifice portion of the device of FIG. 1;

FIG. 1C is a sectional view of a portion of an alternative embodiment including a vented penetrant for use with non-vented rigid containers;

DETAILED DESCRIPTION OF THE INVENTION

Figure 2A:
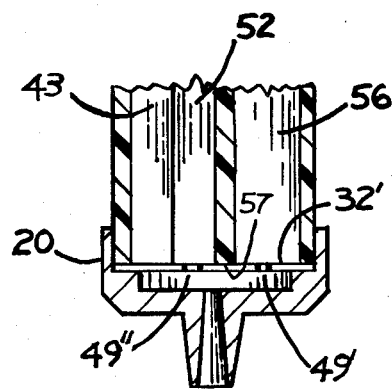
FIG. 2A is an enlarged sectional view of the nozzle and orifice construction of FIG. 2.

Referring to the drawings, a preferred embodiment of the present invention is illustrated in FIGS. 1, 1A and 1B. Specifically, in accordance with and embodying the invention the apparatus represents a flow indicating and metering device for fluid 21 from a supply container (not shown) into the circulatory system of a patient (not shown) by means of infusion needle 45 attached to the outlet of infusion tubing 19. The fluid container is either a flexible bag or vented rigid container for the flow meter administration device generally designated 11.

Specifically, the penetrant 7 defines a passage 8 for liquid flow from the parenteral solution container upon insertion of the penetrant. An alternative penetrant (FIG. 1C) generally designated 40 is for use with non-vented rigid containers. It is provided with a fluid passage 6 for communication with liquid 21 and an atmospheric air vent passage 28 which permits the entrance of air to the supply container as it empties of fluid. Bacterial air filter 5 is located at the entrance of air port 28. Penetrant 7 may also constitute a tubular extension to which may be secured a convenient length of flexible tubing which connects the device 11 to the supply container.

Fluid passage or tube 14 defines an extension of the fluid passage (8 or 6). Its inside diameter is such that liquid readily fills tube 14, expelling air. At the bottom of tube 14 is located a thin orifice disc 32 having an orifice 49 which can be more clearly seen in enlarged FIG. 1B. A flow notch 27 (FIG. 1B) is provided for liquid to enter the bottom of a flow rate indicating tube 18 having an open port 31 and an attached flow rate scale 48. Liquid rises in tube 18 until the liquid surface tension at the small orifice 49 is overcome, at which point flow passes through the orifice and forms drops 29 emerging from a nozzle tip 34. At a constant rate of flow through the device, the liquid 21 reaches a stable height H above the exit of nozzle 34. This liquid level 22 provides an easily read marker along flow rate scale 48 which has calibrated indicia 37 in convenient flow rate units, typically cc per hour.

The diameter of flow indicating tube 18 is preferably sufficiently small, typically about ⅛ inch so that the response time of the liquid column quickly follows any flow changes made by the operator by the use of tubing clamp 42.

The fluid tube 14 and flow indicating tube 18 are enclosed within a drip chamber 12 fitted with a bottom cap 33 containing an outlet which is in communication with outlet tubing 19. The bottom of inflow tube 14 and flow rate indicating tube 18 are sealed by orifice disc 32 and a nozzle cap 20 having a nozzle 34 whose outlet is aligned with orifice 49 of orifice disc 32. The nozzle 34 is not critical to the functioning of the flow meter; however, a preferred form of the flow meter includes a nozzle since an appropriately sized outlet allows discrete, uniform drops of liquid to form and be released so that the zero flow position of liquid level 22 in the flow rate tube 18 remains stable. Also, without the nozzle, the level 22 would tend to fluctuate as each drop is not constant when released from the orifice disc 32 and renders it difficult to obtain an accurate reading.

Also, without a nozzle, because drops of varying size can form, depending on whether the flow meter is completely vertical or tipped at a slight angle, the height at which the liquid reaches in the indicating tube at any established rate will tend to be slightly higher or lower depending on the size of the drop which forms below the orifice. During prolonged intravenous infusion of a solution, the drop size may fluctuate and if adjustments of the flow control clamp are made to bring the fluid level in the indicating tube back to the desired setting, this may result in a departure from the calibrated flow rate.

A well defined nozzle positioned below the orifice will avoid these minor problems. What a nozzle provides besides allowing only drops of uniform size to be formed is to allow the discharge coefficient $C_D$ to be reproducible from flow meter to flow meter. This means that the same calibrations can be applied to all flow meters on their indicating tubes with the assurance each flow meter will deliver the same flow rate at any calibrated setting. The only requirement for the nozzle is that the diameter of the nozzle outlet be at least about twice the diameter of the orifice 49 and concentric to it.

The differential pressure across orifice 49 is always head H, no matter what the air pressure inside the drip chamber 12. Thus, at a constant rate of flow, the flow rate indicating level 22 does not vary nor does it depend upon the amount of liquid remaining in the supply container. Furthermore, changes in back pressure at the needle and raising or lowering of the needle infusion site have no effect on flow rate indication. The inside diameter of indicating tube 18 is of sufficient size that capillary effects are negligible in affecting the air pressure equalization function of port 31. The approximate ⅛ inch diameter not only provides a fast time of response but minimize capillary effects. Thus, a clear, sharp liquid surface 22 results for accurate alignment with the flow rate indicia.

An alternate but not preferred location for the indicia is on the drip chamber 12. A disadvantage is the resulting parallax when viewing the flow rate indicating column.

Fluid notch 27 is used to allow flow to enter indicating tube 18 in a continuous manner from its bottom. This results in a non-fluctuating, stable, indicating level 22. There is no noticeable fluctuation of this level when drops are formed at the nozzle since nozzle flow enters substantially from flow tube 14 as supplied by the reservoir. If however, the fluid tube were not used in such a manner as to provide fluid filling at the base of the indicating tube, and flow were allowed to drip into a larger diameter indicating tube at port 331 instead, a variation in level 22 would be observable since the impingement of drops has disturbed the level's equilibrium. Furthermore, air bubbles could become trapped in the tube. In the embodiment shown in FIG. 1 the set's flow essentially bypasses tube 18 by flowing directly into the nozzle with no noticeable change in head H as drops are formed. It has also been found that this construction avoids air bubbles from forming in the indicating tube at initial set-up since fluid enters from beneath, thereby forcing air bubbles up and out the tube.

As shown in FIG. 1 the unitary construction which includes the penetrant, the two fluid tube passage ways, port 31 and top cap 47 for sealing the drip chamber, lends itself to economical plastic injection molding. Further economics are obtained by employing extruded, transparent tubing for the drip chamber 12 which encloses the flow rate indicating elements in a closed system. A bottom cap 33 is similarly bonded as is the top cap 47, by heat sealing, ultrasonic welding or solvent cementing to the drip chamber. A fluid outlet fitting 35 is provided as part of the bottom cap to accept flexible infusion tubing 19, to which is attached a flow control clamp 42. The clamp regulates the rate of flow of solution to the patient.

Referring now to the orifice disc 32 which is more clearly seen in FIG. 1B, it is sealed to either nozzle cap 20 or circumferentially to fluid tube combination 14 and 18 in a fluid tight fashion. Automated assembly can be accomplished by ultrasonic bonding of the orifice disc 32 into the nozzle cap 20 and then installing the cap onto the fluid tubes.

Alignment problems are minimal since the primary requirement is only that the small orifice hole is positioned in communication with the large bore of nozzle 34. The nozzle cap 20 functions to not only to provide a known size drop for flow rate visualization but captivates and seals the orifice in place.

It can be appreciated that this construction eliminates any flow rate inaccuracy resulting from inaccurate molding of plastic parts. The flow rate sensing element is the stationary thin orifice hole 49 which is dimensionally stable once fabricated.

Referring to the flow rate indicia 37 on the scale, their spacing is basically in accordance with formula (2) supra. Distance H in the first approximation is proportional to the square of flow rate. Thus, equal increments of flow Q are progressively spaced further apart lending the device to higher read out accuracy as full scale flow is approached. This is in contrast to rotameter flowmeter devices using linearly tapered ball or float tubes where scale graduations become progressively closer together at higher rates of flow hindering accurate read out.

According to the present invention there is an expansion of the flow rate scale whereas the rotameter demonstrates a compression. The flow rate indicia spacing has been experimentally determined and is in accordance with formula (2) supra for thin orifices. For thick orifices, viscosity effects are noticeable, and $C_D$ is not a constant value but depends on flow rates and viscosity.

Therefore, equation (2) is not applicable with thick disc orifices.

The scale zero or point of no flow can be adjusted to lie above the top of nozzle cap 20 by proper choice of the diameter of the nozzle 34 which governs the size of drop 29. The smaller the drop size, the higher the scale zero reference mark. For a drop size of typically 20 drops per cc, the scale zero lies approximately 5/16" above the tip of the nozzle. In other words, it requires about 5/16" of head to overcome surface tension forces to form a drop and initiate flow. This value is remarkably constant for most parenteral solutions of widely differing viscosities due to their similarity of surface tension. In industrial applications where substantially larger rates of flow than cc per hour are to be indicated and no drops form but rather a steady stream of flow occurs, the effective scale zero is substantially at the nozzle exit. Provision is then made to extend the scale indicia below that which is shown in FIG. 1A which ends above the nozzle tip.

Figure 2B:
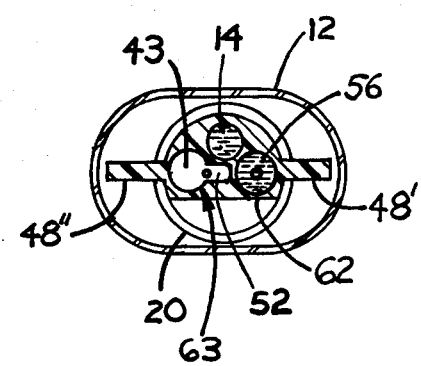
FIG. 2B is a transverse section through the device of FIG. 2 showing in particular the outer drip chamber and inner flow passages.
Figure 2C:
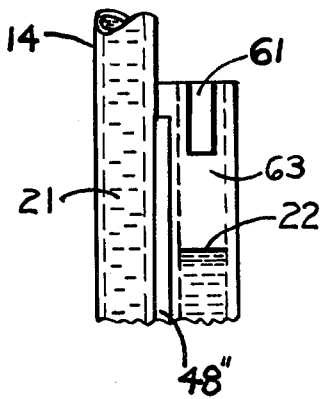
FIG. 2C is a partial side view of the extended flow range device of FIG. 2 showing an air pressure equalization port with fluid overflow capability.
Figure 2:
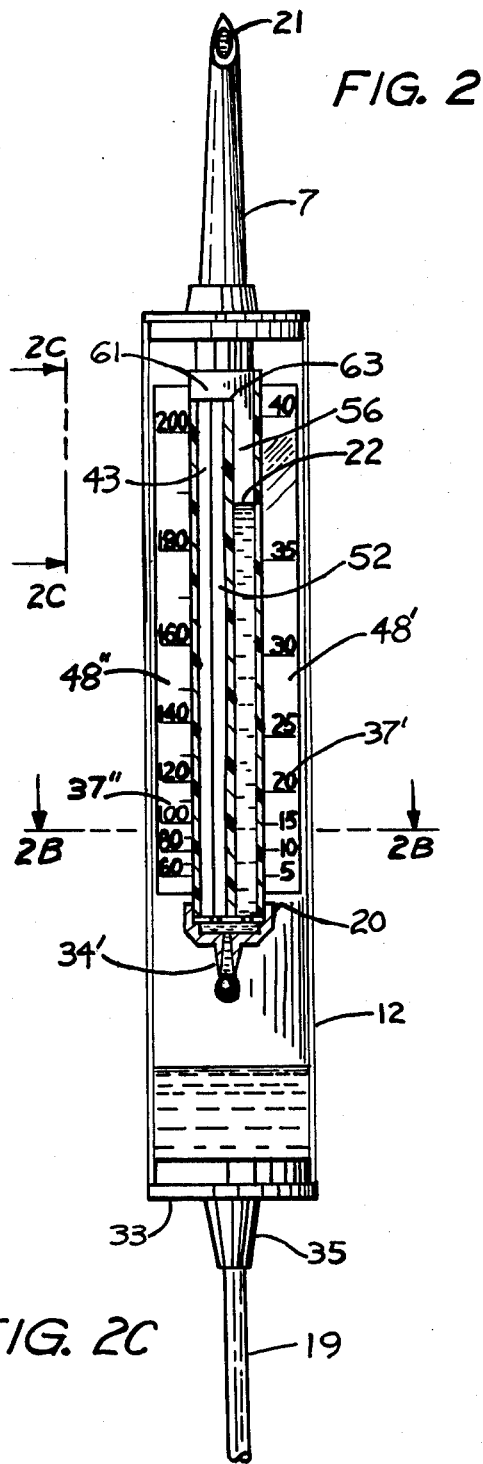
FIG. 2 is a view partially in cross section of an alternative embodiment of the present invention which shows an extended range flow meter device featuring in particular two orifices and two flow meter scales.

FIG. 2 is an alternative embodiment of the present invention which employs two independent orifices and permits an extended range device to be constructed in a compact manner. In this embodiment, at low rates of flow, only liquid indicating tube 56 is filled with liquid to level 22.

Liquid enters the bottom of tube 56 from penetrant tube 14 which is seen in FIG. 2C an in cross section in FIG. 2B. This is accomplished with a connecting slot 27 as explained and shown in the preferred embodiment of FIG. 1B. After passing down tube 14, the liquid begins filling the first flow rate indicating tube 56 and passes through orifice hole 49' in orifice plate 32' as seen in FIG. 2A. Liquid drips off nozzle tip 34'. Liquid will not enter the other orifice 49" because there is virtually no differential pressure developed across this orifice to force liquid in. The nozzle length is made sufficiently long to provide all the head height necessary to form drops, thereby leaving the space immediately below the orifice plate near atmospheric pressure. Any liquid which might enter will only slightly rise in tube 43 and stop.

The diameter of orifice 49' is made relatively small thus providing very fine flow rate reading indicia 37' on scale 48'. As shown in FIG. 2 the maximum capability of the arbitrary scale 48' is only 40 cc per hour which is adequate for pediatric use. When the flow rate to be infused is greater than this, by adjustment of clamp 42 liquid overflows from tube 56 through upper slot 61 (FIG. 2C), thus entering at the open top of second flow tube rate indicating 63 at its right side. The cross section of tube 63 can be seen in FIG. 2B and is shaped into a slot 52 on its right side, which is sufficiently narrow to cause the entering liquid to flow down it without forming air bubbles in the wider tube portion 43. The capillary action of slot 52 keeps the liquid in the slot and allows tube 63 to fill from its bottom. Thus, displaced air passes freely up enlarged section 43 as the indicating liquid level rises. Formation of air bubbles are thus eliminated as the liquid level rises in tube 63 to its equilibrium value. The rate of flow is read off calibrated scale 48" since the first tube 56 is now completely filled and only one level 22 in tube 63 can be read.

By choosing orifice hole 49" larger than orifice 49' a higher capacity flow rate is accomodated on scale 48" in the same set. Indicia 37" are appropriately spaced to read the actual flow observed through the nozzle which is now the combined flow through the orifice holes 49', 49" since they both empty into nozzle cap 20 which serves as a manifold.

If flow rate is now reduced, the level lowers on scale 48". When flow is reduced to below 50 cc per hour for example, tube 43 will empty of liquid and level 22 will then only appear on scale 48' for reading.

If by choice both orifices are of equal size the device is bascially the same as that shown in FIG. 1 but it has been essentially folded. The scale length in other words has been reduced in half, a decided advantage, by providing two parallel flows. The main advantage of this FIG. 2 embodiment however, is that it permits a very accurate scale to be had for the normally used range of flow rates. A different flow capability is provided on the second scale which might be needed in cases of emergency treatment, i.e. cardiac arrest patients where large emergency flows are needed on demand. By choosing the right orifice sizes for orifices 49' and 49" respectively, scale 48' might read from 0 to 300 cc per hour and scale 48" from 300 to 3,000 cc per hour. For other applications such as in industrial use, flow rates of gallons per hour can be provided.

Referring now to FIG. 2B, fluid passage 14 is shown molded integrally with the first flow rate indicating tube 56 and the second flow rate indicating tube passages 43 and 52. Flow rate scales 48" and 48' are also integrally molded. A flat front face 62 is provided which helps viewing the liquid level 22 without distortion in either indicating tube. This embodiment permits easy alignment of respective liquid levels with their scales. Drip chamber 21 may be elliptically shaped to enclose the flow indicating portions and is sealed to the top and bottom caps.

Figure 3:
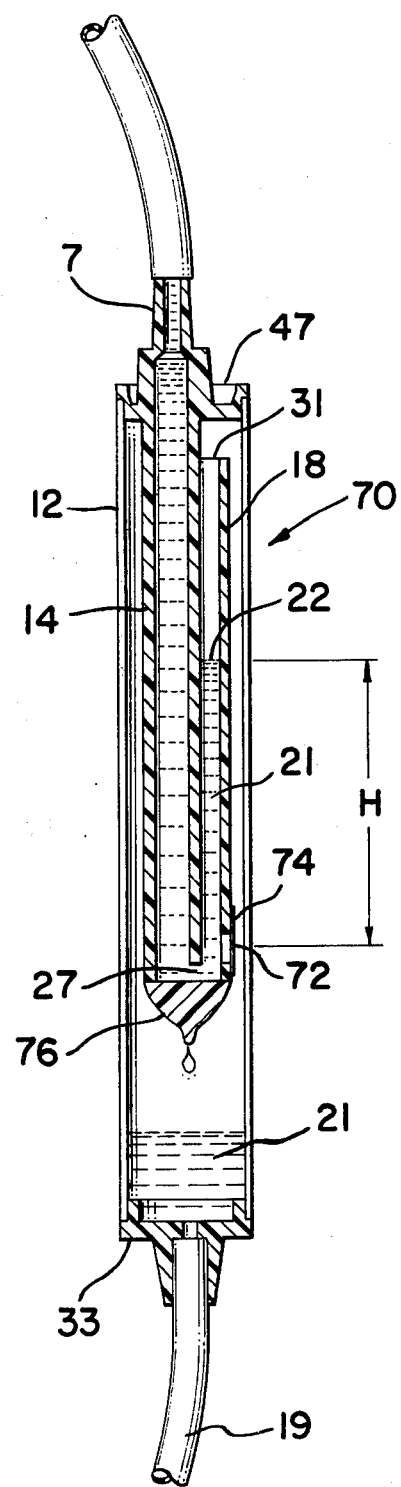
FIG. 3 is a sectional view of still another embodiment of the flow meter device of this invention illustrating a different location for the orifice disc.

Another embodiment of the present invention shown in FIG. 3 illustrates a flow meter 70 wherein the orifice 72 in orifice disc 74 is located on the side at the lower end of flow rate indicating tube 18. Alternatively, disc 74 can be located at a similar position on tube 14. The bottom of tubes 14 and 18 are sealed off by drip tip 76 so that liquid flowing through orifice 72 flows down over drip tip 76 to form discrete drops. In all other respects, the structure of this embodiment is the same as the embodiment of FIG. 1. As in the other embodiments, the orifice disc 74 is quite thin, not more than about 0.015 inch and preferably about 0.001 inch or less, in order to avoid unacceptably high errors in flow rates of solutions having variable viscosities or densities at any particular setting.

Having described the three embodiments, it should be pointed out that the drip chamber in any embodiment is preferably flexible so that by squeezing the chamber initially, air is forced into the supply container and upon release starts the flow of liquid and allows filling of the drip chamber. The liquid 21 must fill infusion tubing 19 before infusion. If a rigid drip chamber is used other initial filling means must be provided. After removal of air from the infusion tubing the rate of flow is conventionally adjusted, using any one of a number of available tubing clamps while simultaneously observing the rate of flow on the flow rate scale.

Although the device herein described is intended to be used by itself in the usual infusion apparatus, it may also be used in series with other flow devices such as electrically driven pumps to monitor or set rate of flow. It may also be used in series with other gravity flow I.V. sets by removal of the flow control clamp. Although only three embodiments of the present invention have been shown, these should not be considered as limiting.

The flow meter principle of employing the liquid column developed across the flow measuring orifice as the flow rate indicating element may be utilized as an internal component in flow metering and regulating systems to indicate flow. In particular, the flow readout elements may be placed internally of and in series with the flow of the FLUID FLOW REGULATOR as described in my patent application Ser. No. 566,076, filed Apr. 8, 1975, now U.S. Pat. No. 3,963,024, which would permit setting of the flow without counting drops.

What is claimed is:

1. A flow meter device including fluid inlet and outlet means comprising:
   (a) a first and a second fluid passage means having upper and lower portions, the upper portion of the first passage means being in communication with the inlet means;
   (b) a passageway interconnecting the lower portions of the first and second passage means;
   (c) a drip chamber enclosing the first and second passage means, the top of said second passage means vented to the drip chamber,
   (d) indicia means associated with the device and adapted for indicating the level of a liquid in the second passage means; the diameter of said second passage means being sufficiently small to give a fast response to changes in flow;
   (e) thin disc means having an orifice and located approximate the lower portions of the first and second passage means and adapted for out flow of liquid from the first and second passage means; the thickness of said orifice is generally in the range of from a fraction of a thousandth of one inch to 0.035 inch for obtaining high flow rate accuracies with fluids of differing kinematic viscosities.

2. The device of claim 1 wherein the orifice disc is located below the passageway between the first and second passage means.

3. The device of claim 2 wherein a nozzle means is associated with the orifice disc, the nozzle means having an outlet at its lower end.

4. The device of claim 3 wherein the cross-sectional area of the nozzle outlet is at least twice the cross-sectional area of the orifice.

5. The device of claim 1 wherein the orifice disc is located on a side wall of a lower portion of the first and second passage means.

6. The flow meter device of claim 1 wherein the thickness of the orifice disc is that which produces an acceptable flow rate error for parenteral solutions with differing kinematic viscosities, the thickness being determined by the equation $$\% \text{ error in flow rate} = 609\, C_D^2 \sqrt{t}/Q\,(\sqrt{v_1} - \sqrt{v_2})$$

where t is expressed in inches.

7. The flow meter of claim 1 having a transparent drip chamber with an outlet and enclosing the first and second conduits; an orifice disc defining an orifice which is located proximate to and below the passageway; and having a nozzle below the orifice disc possessing an opening in liquid communication with the orifice.

8. The flow meter of claim 7 wherein the nozzle opening has a cross-sectional area at least twice the cross-sectional area of the orifice.

9. The flow meter of claim 8 wherein the orifice disc is metallic and is no thicker than about 0.005 inch.

10. A flow meter for liquids comprising a first conduit whose upper end is adapted for communication with a supply container for a liquid, a second conduit with its lower end connected by a passageway to the lower end of the first conduit, a third conduit having its upper end in fluid communication with the upper end of the second conduit, an orifice disc associated with the lower ends of the first, second and third conduits and having a first orifice in communication with the first and second conduits and a second orifice in communication with the third conduit, the thickness of said orifices being generally in the range of from a fraction of a thousandth of one inch to 0.035 inch for obtaining high flow rate accuracies with fluids of differing kinematic viscosities, a drip chamber enclosing the first, second and third conduits and having an outlet, and indicia means associated with the flow meter for measuring levels of liquid in the second or the third conduits.

11. A flow meter device including fluid inlet and outlet means comprising:
   (a) a first, a second, and a third passage means having upper and lower portions, the upper portion of the first passage means being in communication with the inlet means,
   (b) a passageway interconnecting the lower portions of the first and second passage means,
   (c) liquid overflow means providing fluid communication between the upper portions of the second and third passage means,
   (d) thin disc means having an orifice and located approximate the lower portions of the first and second passage means and adapted for outflow of liquid from the first and second passage means,
   (e) a second thin disc means having an orifice and located at the bottom of said third passage means for permitting the flow of liquid from the third passage means when liquid occupies the third passage means, and
   (f) the thickness of said orifice is generally in the range of from a fraction of a thousandth of one inch to 0.035 inch of differing kinematic viscosities.

* * * * *